(12) United States Patent
Karlsson et al.

(10) Patent No.: US 12,213,943 B2
(45) Date of Patent: Feb. 4, 2025

(54) CONNECTOR FOR A MEDICAL CONTAINER

(71) Applicant: Fresenius Kabi AB, Uppsala (SE)

(72) Inventors: Lars Karlsson, Älvsjö (SE); Torsten Brandenburger, Reichelsheim (DE)

(73) Assignee: Fresenius Kabi AB, Uppsala (SE)

( * ) Notice: Subject to any disclaimer, the term of this patent is extended or adjusted under 35 U.S.C. 154(b) by 0 days.

(21) Appl. No.: 18/217,804

(22) Filed: Jul. 3, 2023

(65) Prior Publication Data
US 2023/0338236 A1 Oct. 26, 2023

Related U.S. Application Data

(63) Continuation of application No. 15/572,550, filed as application No. PCT/EP2016/059897 on May 3, 2016, now abandoned.

(30) Foreign Application Priority Data

May 8, 2015 (EP) .................................... 15166901

(51) Int. Cl.
| | |
|---|---|
| *A61J 1/14* | (2023.01) |
| *A61J 1/10* | (2006.01) |
| *A61J 1/18* | (2023.01) |
| *A61M 39/20* | (2006.01) |

(52) U.S. Cl.
CPC ............... *A61J 1/1475* (2013.01); *A61J 1/10* (2013.01); *A61J 1/18* (2013.01); *A61J 1/1425* (2015.05); *A61M 39/20* (2013.01)

(58) Field of Classification Search
CPC .... A61J 1/1475; A61J 1/10; A61J 1/18; A61J 1/1425; A61J 1/1406; A61J 1/2065; A61J 1/2027; A61M 39/20
See application file for complete search history.

(56) References Cited

U.S. PATENT DOCUMENTS

| | | | | |
|---|---|---|---|---|
| 5,088,996 A | * | 2/1992 | Kopfer | A61J 1/2096 141/330 |
| 5,827,262 A | * | 10/1998 | Neftel | A61J 1/2096 604/82 |
| 7,354,426 B2 | | 4/2008 | Young | |

(Continued)

FOREIGN PATENT DOCUMENTS

| | | |
|---|---|---|
| CN | 1655750 A | 8/2005 |
| CN | 1767799 A | 5/2006 |

(Continued)

*Primary Examiner* — Kai H Weng
*Assistant Examiner* — Alessandro R Del Priore
(74) *Attorney, Agent, or Firm* — Blank Rome LLP

(57) ABSTRACT

A connector for a medical container is described. The connector includes a connector element defining an inner lumen extending axially from a first end of the connector element to a second end of the connector element that is opposite the first end. The connector element includes a fastening section at the first end of the connector element that is secured to the medical container, a pinch-off section extending from the fastening section towards the second end of the connector element, a head section extending from the pinch-off section towards the second end of the connector element, and a deflection element extending from the head section towards the first end of the connector element.

17 Claims, 5 Drawing Sheets

(56) References Cited

U.S. PATENT DOCUMENTS

| | | | |
|---|---|---|---|
| 8,162,915 B2* | 4/2012 | Brandenburger | A61J 1/1475 |
| | | | 604/403 |
| 2003/0075469 A1* | 4/2003 | Herbert | A61J 1/10 |
| | | | 206/438 |
| 2004/0199139 A1* | 10/2004 | Fowles | A61J 1/2089 |
| | | | 604/414 |
| 2005/0059951 A1 | 3/2005 | Young | |
| 2008/0262466 A1* | 10/2008 | Smith | B65D 51/002 |
| | | | 215/247 |
| 2013/0102990 A1* | 4/2013 | Domkowski | A61J 1/2089 |
| | | | 604/416 |

FOREIGN PATENT DOCUMENTS

| | | |
|---|---|---|
| DE | 10313760 B3 | 6/2004 |
| WO | 2003099191 A1 | 12/2003 |
| WO | 2004084793 A1 | 10/2004 |
| WO | 2006071781 A2 | 7/2006 |

* cited by examiner

CONNECTOR FOR A MEDICAL CONTAINER

CROSS REFERENCE TO RELATED APPLICATIONS

This application is a continuation application of U.S. patent application Ser. No. 15/572,550, filed Nov. 8, 2017, which is a U.S. National Phase Application under 35 USC 371 of International Application No. PCT/EP2016/059897, filed May 3, 2016, which claims the benefit of the priority date of European Patent Application No. 15166901.7, filed May 8, 2015, the contents of the aforementioned applications are incorporated herein in their entirety.

BRIEF SUMMARY OF THE DISCLOSURE

The invention relates to a connector for a medical container according to the preamble of claim 1.

A connector of this kind comprises a connector element to be attached to the medical container for providing a port to the medical container. The connector element comprises a head section and a pinch-off section adjoining the head section, wherein the head section comprises an opening and the pinch-off section encloses an inner lumen being in fluid connection with the opening of the head section for providing a fluid path through the connector element. The opening of the head section can be closed by a closure element which is attachable to the head section of the connector element such that, when the closure element is attached to the head section, the fluid path through the connector element is blocked. A membrane element can be placed in-between the closure element and the head section of the connector element. The membrane element can be pierced by a needle of a delivery device, for example a syringe, for injecting a medical fluid into the medical container or for extracting a medical fluid from the medical container.

The connector, when attached to a medical container, shall allow for filling the medical container with a medical fluid, for example a fluid for the parenteral feeding of a patient such as a glucose solution, a fat solution or an amino acid solution. The medical container herein may be filled for example by a medical supplier (which may be the container manufacturer) or in a pharmacy of a hospital and shall subsequently be prepared such that it can be stored and delivered for a later usage.

For filling the container, as it is described in WO 2004/084793 A1, a filling spike of a filling station may be inserted into the connector element prior to attaching the closure element to the connector element. After the filling is completed, the connector element is pinched-off at its pinch-off section such that the fluid path through the connector element is closed and fluid cannot exit from the medical container through the connector element. By attaching the closure element to the head section of the connector element, then, the connector element is sealed towards the outside such that the pinching of the pinch-off section can be released, and the medical container can be stored or delivered to a hospital or the like.

When using the medical container on a patient, the closure element may be opened, for example by breaking-off a break-off part. A user hence may access the connector element by piercing the membrane element placed in-between the head section of the connector element and the closure element using for example a needle of a syringe. In this way, fluid may be extracted from the medical container, or fluid may be added to the medical container in order to for example add further components such as vitamins or other nutritional components or the like to the fluid contained in the container.

When piercing the membrane element using a needle, it shall be avoided that the needle comes into contact with the pinch-off section of the connector element, e.g., because the pinch-off section could have a reduced wall thickness in order for it to be deformable for pinching off the connector element. If the needle were to come into contact with the pinch-off section, there may be a risk of damaging the pinch-off section, possibly rendering the medical container unsterile and hence useless. It is clear that the invention relates to any kind of pinch-off section being in the danger to be damaged by the needle. Reasons therefore may the thickness of the wall, selection of material of the wall or other. The invention will be described by a connector with thinner walls at the pinch-off section in way of example only.

It is an object of the invention to provide a connector for a medical container which in an easy and cost-efficient manner reduces the risk of damaging the pinch-off section of the connector element when piercing the membrane element by means of a needle.

This object is achieved by means of a connector comprising the features of the independent claims.

Accordingly, a deflection element is provided which extends from the head section towards the inner lumen of the pinch-off section for deflecting a needle of a delivery device when piercing the membrane element.

The deflection element serves to guide the needle towards the inner lumen of the pinch-off section when piercing the membrane element by means of the needle. The deflection element herein is shaped such that the risk for damaging the pinch-off section by means of the needle, when introducing it into the connector element, is reduced, in particular in that the needle is guided such that it would not come into contact with the walls of the pinch-off section.

In one embodiment, the deflection element reaches into the inner lumen of the pinch-off section. The deflection element hence extends from the head section and reaches into the inner lumen enclosed by the pinch-off section. Herein, the deflection element is formed as a comparatively rigid piece and in particular may be formed in one piece with the head section. When a needle is inserted into the opening of the head section, it is deflected by the deflection element or is stopped by the deflection element such that the needle cannot come into contact with the walls of the pinch-off section.

Although the deflection element may reach into the inner lumen of the pinch-off section, it extends into the inner lumen of the pinch-off section only that far that a pinching off of the pinch-off section is not hindered. In particular, the deflection element does not extend into a region of the pinch-off section in which (typically) a pinching off shall take place.

The deflection element may for example have the shape of a cylindrical pipe. The deflection element extends from the head section and provides a guide for the needle such that the needle cannot come into contact with walls of the pinch-off section when inserting it into the connector element.

In one embodiment, the deflection element, for example having the shape of a cylindrical pipe, comprises a guide opening through which the needle may be guided. The guide opening longitudinally extends along an insertion direction along which the needle of the delivery device can be inserted into the connector element. Along the insertion direction, the guide opening beneficially is aligned with the opening of the head section of the connector element through which the needle of the delivery device is inserted into the connector element.

The deflection element, in one embodiment, is arranged at a radial distance to the walls of the pinch-off section. The deflection element, hence, is arranged radially inside the pinch-off section such that it provides a guide inside of the pinch-off section. Because the walls of the pinch-off section are arranged radially outside of the deflection element at a radial distance to the deflection element, a needle guided by the deflection element cannot come into contact with the walls of the pinch-off section such that the risk for damaging the walls of the pinch-off section when inserting the needle into the connector element is greatly reduced.

The connector element may for example have the shape of a ship-shaped conus. The connector element hence has a general ship shape and comprises for example a fastening section which can be inserted in-between foils of the medical container such that the connector element via its fastening section can be welded to the foils of the medical container (having the shape of for example a flexible bag). Herein, the fastening section has a rather rigid shape and has an increased wall thickness in comparison to walls of the pinch-off section. Because the walls of the pinch-off section have a reduced wall thickness (at least in particular regions), the pinch-off section is flexibly deformable for pinching-off the fluid path through the connector element after filling the medical container.

The closure element may for example comprise an attachment section attachable to the head section of the connector element and a break-off part connected to the attachment section along a break line along which the break-off part can be broken off the attachment section. The closure element may for example be attached to the connector element after filling of the medical container such that, with the closure element attached, the medical container can be stored or delivered for example to a hospital. When a user wants to access the medical container for example to inject a medical fluid into the medical container or to extract a medical fluid from the medical container, he breaks off the break-off part and hence opens the connector element such that the membrane element placed in-between the closure element and the connector element is accessible from the outside for piercing it by means of a needle of a suitable delivery device, for example a syringe or the like.

BRIEF DESCRIPTION OF THE DRAWINGS

The idea underlying the invention shall subsequently be described in more detail with reference to the embodiments shown in the figures. Herein.

DETAILED DESCRIPTION OF THE DISCLOSURE

Figure 1:
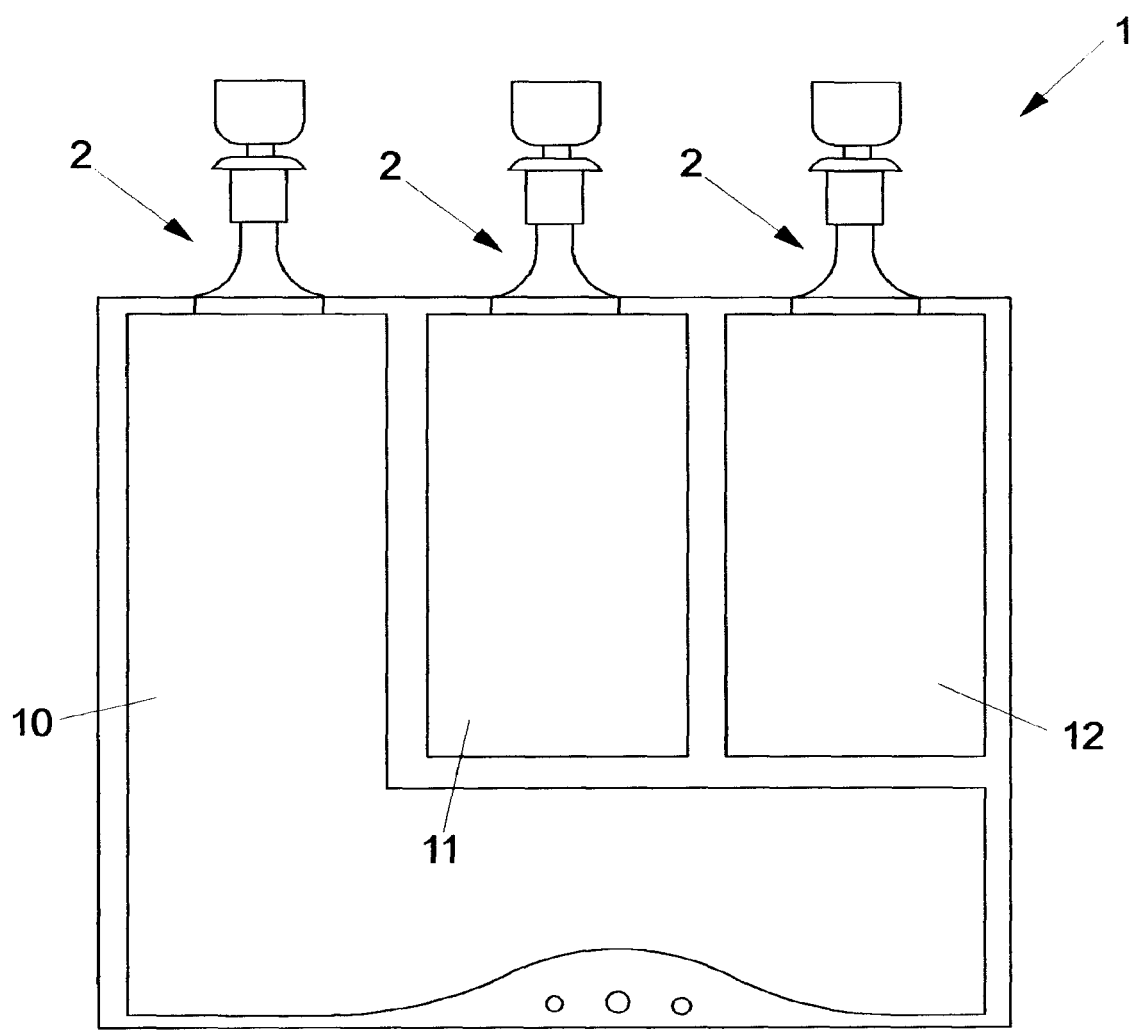
FIG. 1 shows a schematic view of a medical container in the shape of a three-chamber flexible bag comprising three connectors.

FIG. 1 shows in a schematic view a medical container 1 in the shape of a flexible bag made of thin, flexible foils welded to each other. The medical container 1, in the shown embodiment, comprises three chambers 10-12 for receiving medical fluids, for example for the parenteral feeding of a patient. The chambers 10-12 herein may contain different medical fluids, for example a glucose solution, a fat solution and an amino acid solution, wherein the chambers 10-12 may be connected via tearable seams which may be torn open to bring the chambers 10-12 in fluid connection with each other for mixing the different solutions with each other prior to delivering them to a patient.

Each chamber 10-12 is associated with a connector 2, as shown in FIG. 1. The chambers 10-12 herein are filled via their respective connectors 2, for example by a medical supplier or within a hospital pharmacy or the like. After the chambers 10-12 have been filled, the connectors 2 are closed such that the chambers 10-12 are sealed towards the outside and the medical container can be stored or delivered for use on a patient. The mixing of the different solutions contained in the chambers 10-12 then takes place immediately prior to injecting the medical fluid of the medical container 1 to a patient in that a user, for example a nurse, tears open the tearable seams in-between the chambers 10-12 such that the solutions contained in the chambers 10-12 can mix within the medical container 1.

Figure 4A:
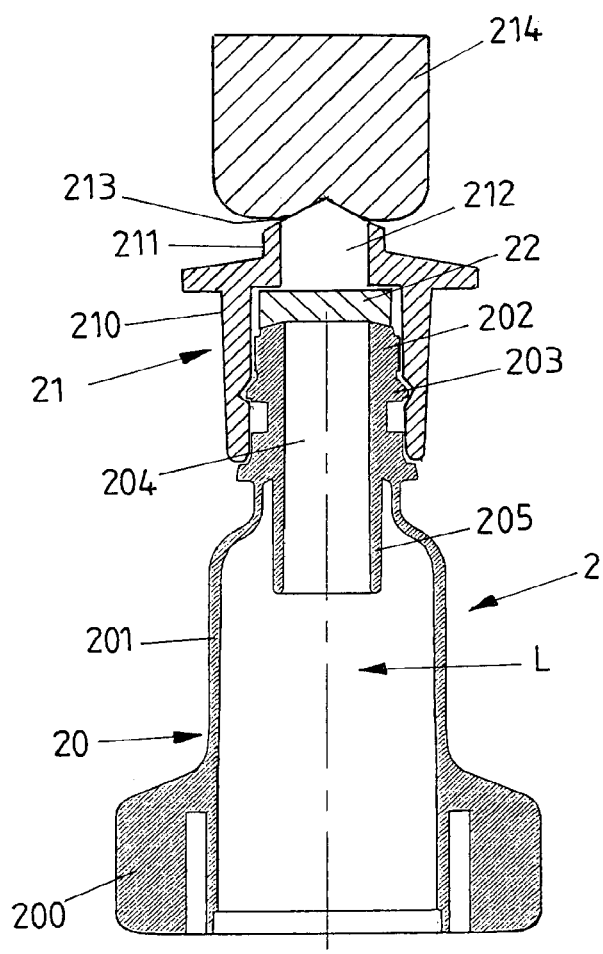
FIG. 4A shows a sectional view of the connector element with a closure element attached to a head section of the connector element.
Figure 4B:
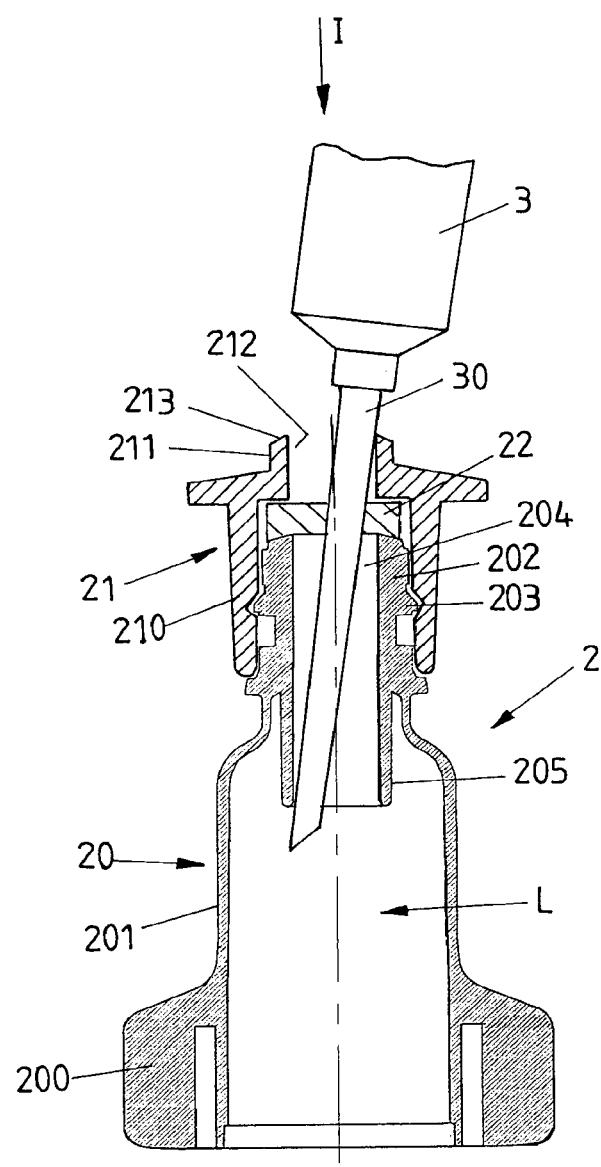
FIG. 4B shows the view of FIG. 4A, with a break-off part broken off the closure element and with a needle of a delivery device inserted into the connector element.

As shown in FIGS. 4A and 4B, each connector 2 comprises a connector element 20, a closure element 21 and a membrane element 22 placed in-between the closure element 21 and the connector element 20.

Detailed views of the connector element 20 are provided in FIGS. 2A to 2C and 3A and 3B. The connector element 20 comprises a fastening section 200 which can be inserted in-between foils of the medical container 1 for welding the connector element 20 to the medical container 1. The fastening section 200 is adjoined by a pinch-off section 201, which terminates in a head section 202. To the head section 202 the closure element 21 is attached via an attachment section 210 in a form locking manner by engaging with a locking rim 203 of the head section 202.

The closure element 21, when it is attached to the head section 202 of the connector element 20, closes off an opening 204 in the head section 202. The closure element 21 comprises a head section 211 adjoining the attachment section 210 and being connected, in the state of FIG. 4A, to a break-off part 214 along a circumferential break line 213.

For manufacturing the medical container 1, the connector elements 20 of the connectors 2 are placed in-between the foils of the medical container 1 and are welded to the foils when forming the chambers 10-12 of the medical container 1. After completion of the manufacturing, the chambers 10-12 of the medical container 1 are filled for example by a medical supplier or in a pharmacy of a hospital by inserting a filling spike into the respective connector elements 20 and by filling the chambers 10-12 with medical solutions as desired.

Figure 3A:
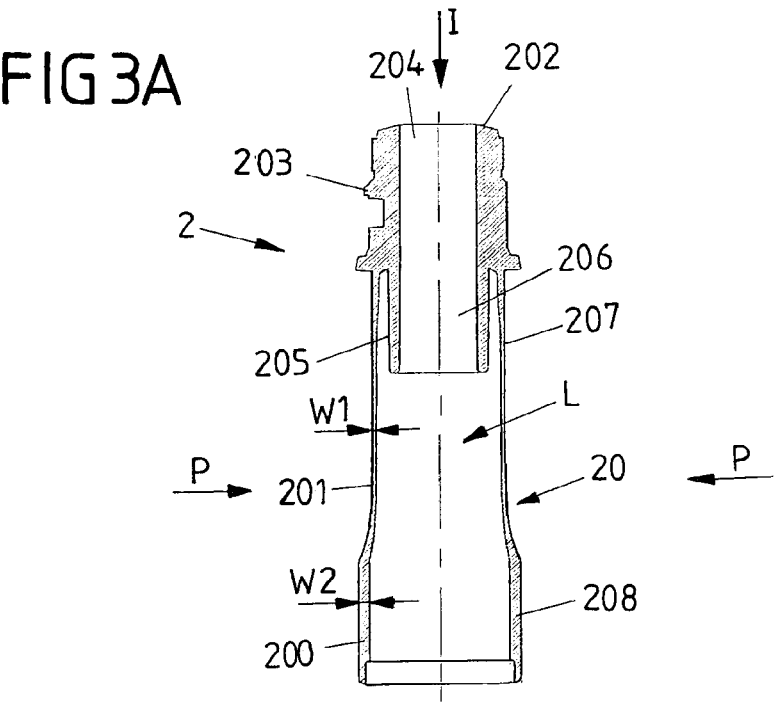
FIG. 3A shows a sectional view along line A-A according to FIG. 2A.
Figure 3B:
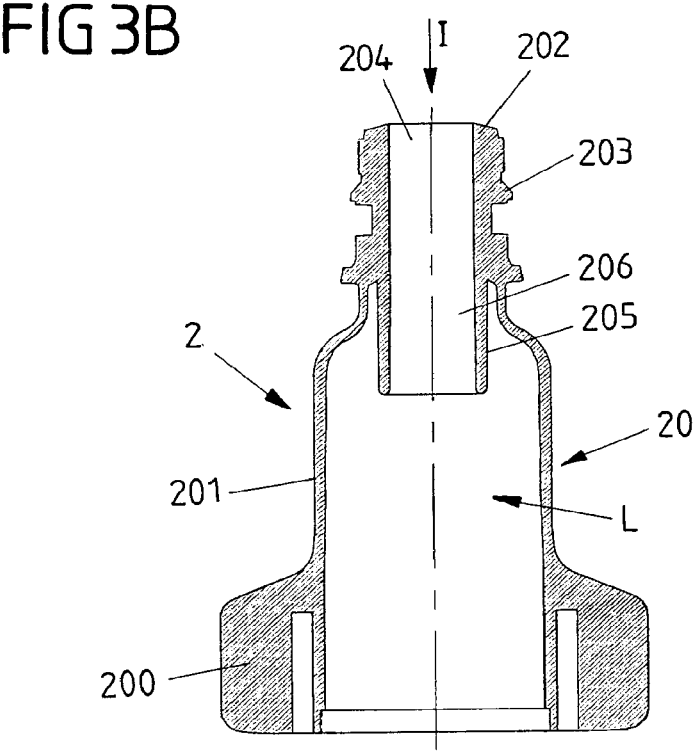
FIG. 3B shows a sectional view along line B-B according to FIG. 2B.

Once a chamber 10-12 has been filled, the respective connector element 20 is pinched-off at its pinch-off section 201 by applying a suitable clamping device. For this, the connector element 20 is flexibly deformable at its pinch-off section 201, which comprises a reduced wall thickness W1 in comparison to other sections of the connector element 20, for example in comparison to a wall thickness W2 of the walls 208 of the fastening section 201, as depicted in FIG. 3A.

By pinching off the connector element 20 at its pinch-off sections 201, a fluid path through the connector element 20 is blocked in that an inner lumen L enclosed by the pinch-off section 201 is pinched-off. Subsequently, the closure element 21 can be attached to the head section 202 of the connector element 20 for closing the connector element 20, and the pinching of the pinch-off section 201 can be released.

After all chambers 10-12 have been filled and respective closure elements 21 have been attached to the connector elements 20 of the connectors 2, the medical container 1 can be stored or can be delivered to a place of usage, for example to a hospital.

Once the medical solution contained in the medical container 1 shall be administered to a patient, a user may break off one or multiple of the break-off parts 214 of the closure elements 21 of the connectors 2 and may insert a needle 30 of a suitable delivery device 3, for example a syringe, into an opening 212 within the head section 211 of the closure element 21 and may pierce the membrane element 22 held in-between the closure element 21 and the connector element 20. By piercing the membrane element 22 by means of the needle 30 and by inserting the needle 30 in an insertion direction I into the connector element 20 through the opening 204 of the head section 202 of the connector element 20, a medical fluid may be added to the medical container 1 or a medical fluid may be extracted from the medical container 1. For example, if the medical container 1 comprises different solutions for the parenteral feeding of a patient, further components such as vitamins or the like may be added via one of the connectors 2 prior to administering the (mixed) solutions to a patient.

The membrane element 22 is constituted as a self-sealing membrane which, after removing the needle 30 of the delivery device 3, seals itself such that the connector element 20 is closed in a fluid-tight manner towards the outside.

When inserting the needle 30 of the delivery device 3 through the head section 202 of the connector element 20 towards the inner lumen L enclosed by the pinch-off section 201, it shall be avoided that the needle 30 pierces the walls 207 of the pinch-off section 201 (having a reduced wall thickness W1 as shown in FIG. 3A). For this, a deflection element 205 having the shape of a cylindrical pipe is provided which extends from the head section 202 towards the inner lumen L of the pinch-off section 201, as shown in the sectional views of FIGS. 3A and 3B. The deflection element 205 comprises a longitudinal guide opening 206 which is aligned along the insertion direction I with the opening 204 of the head section 202 such that the needle 30 of a delivery device 3 is guided via the deflection element 205 towards the inner lumen L of the pinch-off section 201, as shown in FIG. 4B.

The deflection element 205 in the shape of a cylindrical pipe is formed in one piece with the connector element 20 and has a rigid shape such that a needle 30 pinching onto the inner circumferential face of the guide opening 206 is deflected and guided in the insertion direction I or is stopped such that it cannot come into contact with the outer walls 207 of the pinch-off section 201. Hence, the risk that the walls 207 of the pinch-off section may be damaged by the needle 30 is reduced.

The deflection element 205 extends from the head section 202 in the insertion direction I and reaches into the inner lumen L of the pinch-off section 201. It herein is placed inside the pinch-off section at a radial distance to the walls 207.

Although the deflection element 205 reaches into the inner lumen L of the pinch-off section 201, it does not extend through the pinch-off section 201 and in particular reaches into the inner lumen L only that far that a reliable pinching of the pinch-off section 201 is not hindered.

Figure 2A:
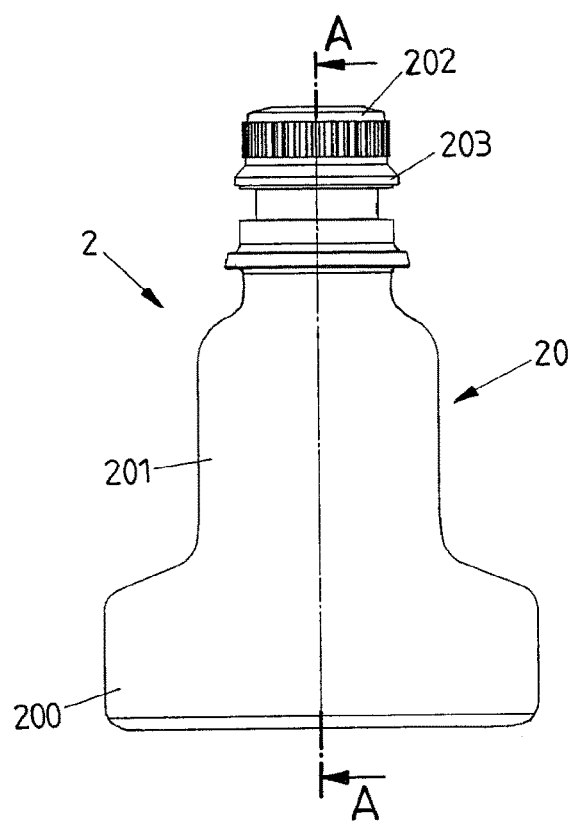
FIG. 2A shows a front view of a connector element of a connector.
Figure 2B:
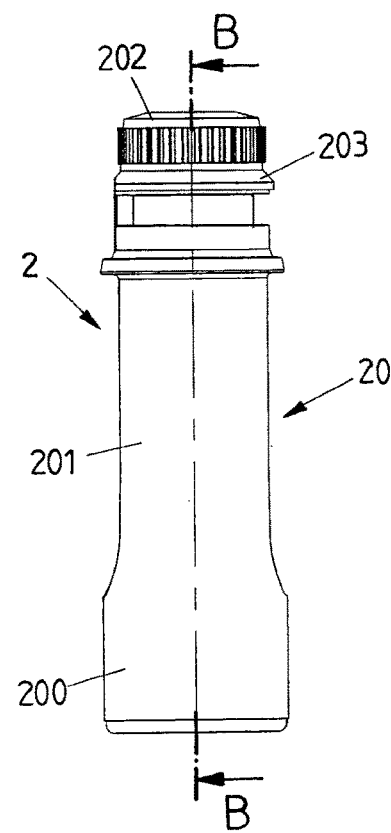
FIG. 2B shows a side view of the connector element.
Figure 2C:
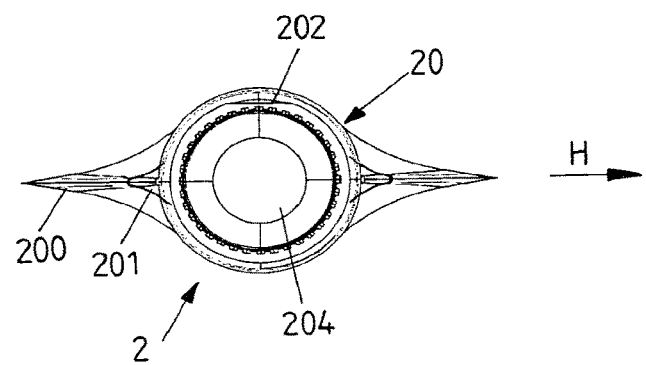
FIG. 2C shows a top view of the connector element.

The connector element 20, as visible from the top view of FIG. 2C, has the general shape of a ship, with the fastening section 200 reducing in width towards both sides along a horizontal direction H such that the fastening section 200 may be reliably welded to the foils of the medical container 1 for providing a fluid-tight transition. The pinch-off section 201 likewise does not have a circular cross-section, but is formed such that it may be reliably pinched-off in a pinch-off direction P (see FIG. 3A) for closing off the fluid path through the connector element 20, as it is described for example in WO 2004/084793 A1.

The invention is not limited to the embodiments described above, but may be implemented in an entirely different fashion.

In particular, the invention is not limited to three-chamber medical bags, but may be applied to any sort of medical containers, having one, two or more chambers.

The medical container not necessarily is flexible, but may also have a rigid shape, such as the shape of a bottle or the like.

Each chamber of the medical container may be provided with one, two or more connector(s) according to the present invention. It is also understood that the medical container may provided with a mixture of both, inventive connector(s) and connector(s)/port(s) of the prior art, depending on the needs for the use of said container.

LIST OF REFERENCE NUMERALS

1 Medical container (bag)
10-12 Chamber
2 Connector
20 Connector element
200 Fastening section
201 Pinch-off section
202 Head
203 Locking rim
204 Opening
205 Deflection element
206 Guide opening
207, 208 Walls
21 Closure element
210 Attachment section
211 Head section
212 Opening
213 Break line
214 Break-off part
22 Membrane
3 Delivery device
Needle
H Horizontal direction
I Insertion direction
L Inner lumen
P Pinch-off direction
W1, W2 Wall thickness

The invention claimed is:

1. A connector for a medical container, the connector comprising:
   a connector element defining an inner lumen extending along an axis from a first end of the connector element to a second end of the connector element that is opposite the first end, the connector element comprising:
      a fastening section at the first end of the connector element, the fastening section configured to be secured to the medical container;
      a pinch-off section extending from the fastening section towards the second end of the connector element;
      a head section extending from the pinch-off section towards the second end of the connector element, wherein the head section comprises:
         a locking rim, and
         another rim that extends radially beyond the locking rim, the another rim being closer to the first end of the connector element than the locking rim; and
      a deflection element directly connected to and extending from the head section another rim towards the first end of the connector element, wherein:
         the deflection element does not axially overlap with the head section,
         the deflection element is radially spaced from and within a wall of the pinch-off section,
         an end of the deflection element axially terminates at a point far enough into a first portion of the inner lumen defined by the pinch-off section so that a needle inserted through the head section cannot come into contact with the wall of the pinch-off section so as to protect the pinch-off section, and
         the deflection element does not axially overlap with a second portion of the pinch-off section so as not to hinder pinching of the pinch-off section;
   a closure element configured to lock to the locking rim of attach to the head section and that axially terminates at the another rim of the head section when the closure element is locked to at the second end of the connector element; and
   a membrane element between the connector element and the closure element, the membrane element configured to seal the inner lumen.

2. The connector of claim 1, wherein the deflection element does not axially overlap with the closure element.

3. The connector of claim 1, further comprising a break-off part extending from the closure element.

4. The connector of claim 1, wherein the membrane element is a self-sealing membrane.

5. The connector of claim 1, wherein the deflection element is cylindrically-shaped.

6. The connector of claim 1, wherein the pinch-off section is flexibly deformable for pinching off the inner lumen.

7. The connector of claim 1, wherein a central axis of a lumen defined by the deflection element is aligned with a central axis of the first portion of the inner lumen defined by the head section.

8. The connector of claim 1, wherein the connector element is integrally formed as one piece.

9. The connector of claim 1, wherein the fastening section is configured to be welded between two layers of the medical container to be secured to the medical container.

10. The connector of claim 1, wherein the deflection element guides the needle inserted into the inner lumen.

11. The connector of claim 1, wherein the second portion of the pinch-off section is closer to the first end of the connector element than the second portion of the pinch-off section.

12. The connector of claim 1, wherein:
   the pinch-off section is connected to and extends from the head section to extend between the head section and the fastening section, and
   wherein an outer diameter of the pinch-off section connected to the head section is smaller than an outer diameter of the pinch-off section connected to the fastening section.

13. The connector of claim 4, wherein the pinch-off section defines a shoulder closer to the head section than the fastening section.

14. A connector for a medical container, the connector comprising:
   a connector element defining an inner lumen extending axially from a first end of the connector element to a second end of the connector element that is opposite the first end, the connector element comprising:
      a fastening section at the first end of the connector element, the fastening section configured to be secured to the medical container;
      a pinch-off section extending from the fastening section towards the second end of the connector element;
      a head section extending from the pinch-off section towards the second end of the connector element, wherein the head section comprises:
         a locking rim, and
         another rim that extends radially beyond the locking rim, the another rim being closer to the first end of the connector element than the locking rim;
      a deflection element directly connected to and extending from the another rim towards the first end of the connector element,
      wherein the deflection element terminates at an end that extends into a portion of the inner lumen defined by the pinch-off section to protect the pinch-off section without hindering pinching of the pinch-off section; and
   a closure element configured to lock to the locking rim of the head section and that axially terminates at the another rim of the head section when the closure element is locked to the connector element.

15. The connector of claim 14, wherein the deflection element is radially spaced from and within a wall of the pinch-off section.

16. The connector of claim 14, further comprising a membrane element between the connector element and the closure element, the membrane element configured to seal the inner lumen.

17. The connector of claim 14, wherein the deflection element does not axially overlap with the head section.

* * * * *